United States Patent [19]

Lerman et al.

[11] Patent Number: 5,224,486
[45] Date of Patent: Jul. 6, 1993

[54] METHOD AND APPARATUS FOR CLASSIFYING HEARTBEAT WAVEFORMS

[75] Inventors: David J. Lerman, McMinnville; Collin M. Portnuff, Tualatin; Matthew S. Glei, McMinnville, all of Oreg.

[73] Assignee: Hewlett-Packard Company, Palo Alto, Calif.

[21] Appl. No.: 843,490

[22] Filed: Feb. 28, 1992

[51] Int. Cl.$^5$ ............................................ A61B 5/0402
[52] U.S. Cl. ...................................... 128/696; 128/710
[58] Field of Search ......................... 128/696, 710, 712

[56] References Cited

U.S. PATENT DOCUMENTS 3,874,370 4/1975 Harris et al. .......................... 128/712
4,896,677 1/1990 Kaneko et al. ....................... 128/696
4,964,410 10/1990 Leahey et al. ....................... 128/696

Primary Examiner—Kyle L. Howell
Assistant Examiner—Scott M. Getzow

[57] ABSTRACT

A computer controls a video display having a display screen for displaying ECG heartbeats superimposed over one another. The ECG data is collected during Holter monitoring and stored in a memory. The Holter monitor preliminarily classifies each beat to a morphology. A representative sample of each morphology is presented in a display window. Each sample can be overlaid with any other selected sample, in different colors, in a compare window having an enlarged scale from the display windows. After comparison, different morphologies can be merged and a selected beat classification can be reclassified to another morphology.

20 Claims, 6 Drawing Sheets

5,224,486

METHOD AND APPARATUS FOR CLASSIFYING HEARTBEAT WAVEFORMS

BACKGROUND OF THE INVENTION

1. Field of the Invention

The present invention relates generally to methods and apparatus for analyzing stored ECG data and more particularly to such methods and apparatus which facilitate classifying the morphologies of a plurality of ECG heartbeat waveforms.

2. Description of the Related Art

In a Holter ECG monitoring system, a patient is fitted with a monitor which detects and stores continuous ECG waveforms. Sometimes several leads are connected to the patient so that two or more such waveforms are recorded. It is not unusual for such a monitor to be worn for many hours thereby generating thousands of periodic heartbeat waveforms which are stored for later review to assist in diagnosis and treatment of the patient.

Some Holter monitors include processors which automatically classify each heartbeat waveform into similar shapes or morphologies, and also identify a typical heartbeat waveform example from each morphology. After the data is collected and transferred to a system for displaying the ECG waveform, a clinician examines the example selected by automated analysis. The role of the clinician is to further group them into a minimal set of clearly-different morphologies. The clinician must examine each of the representative heartbeat waveforms provided by the Holter monitoring system and determine which are truly different and which are generally the same. Typically the clinician merges some of the morphologies as being substantially the same and, in addition, reclassifies other morphologies. For example, a morphology identified as a ventricular ectopic beat may be reclassified by the clinician as actually representing an artifact or some other beat classification.

Prior art systems provide a matrix of adjacent display screens each of which displays a heartbeat representative of a different morphology as determined by the Holter monitor. In some prior art systems, one of the representative heartbeat waveforms can be selected to be overlaid on another heartbeat waveform to facilitate comparison. Even so, it is difficult for a clinician to compare a number of ECG heartbeat waveforms, especially when they initially appear relatively similar to one another, and thereafter merge or reclassify the various morphologies.

SUMMARY OF THE INVENTION

A method for classifying heartbeat waveforms contained in stored ECG data in which a heartbeat waveform is displayed in each of a plurality of display windows. Two of the display windows are selected and the heartbeat waveforms therein are displayed superimposed in a separate compare window. Thereafter a heartbeat waveform in one of the selected windows is classified.

The present invention is advantageous in that it provides a separate compare window having a larger scale than the windows displaying each of the individual morphologies. The ability to see heartbeat waveforms adjacent the representative waveform aids in morphology classification. Each of the overlaid waveforms have their R-waves aligned. In addition, the overlaid waveforms are each displayed in a different color, thereby further facilitating a clinician's ability to compare the waveforms. Subsequent reclassification or merging of morphologies is rapidly and easily accomplished. Selected display windows are highlighted thereby providing a quickly-recognizable visual indication of which morphologies are being compared in the compare window.

The foregoing and other objects, features and advantages of the invention will become more readily apparent from the following detailed description of a preferred embodiment which proceeds with reference to the drawings.

DETAILED DESCRIPTION OF THE PREFERRED EMBODIMENT

Figure 1:
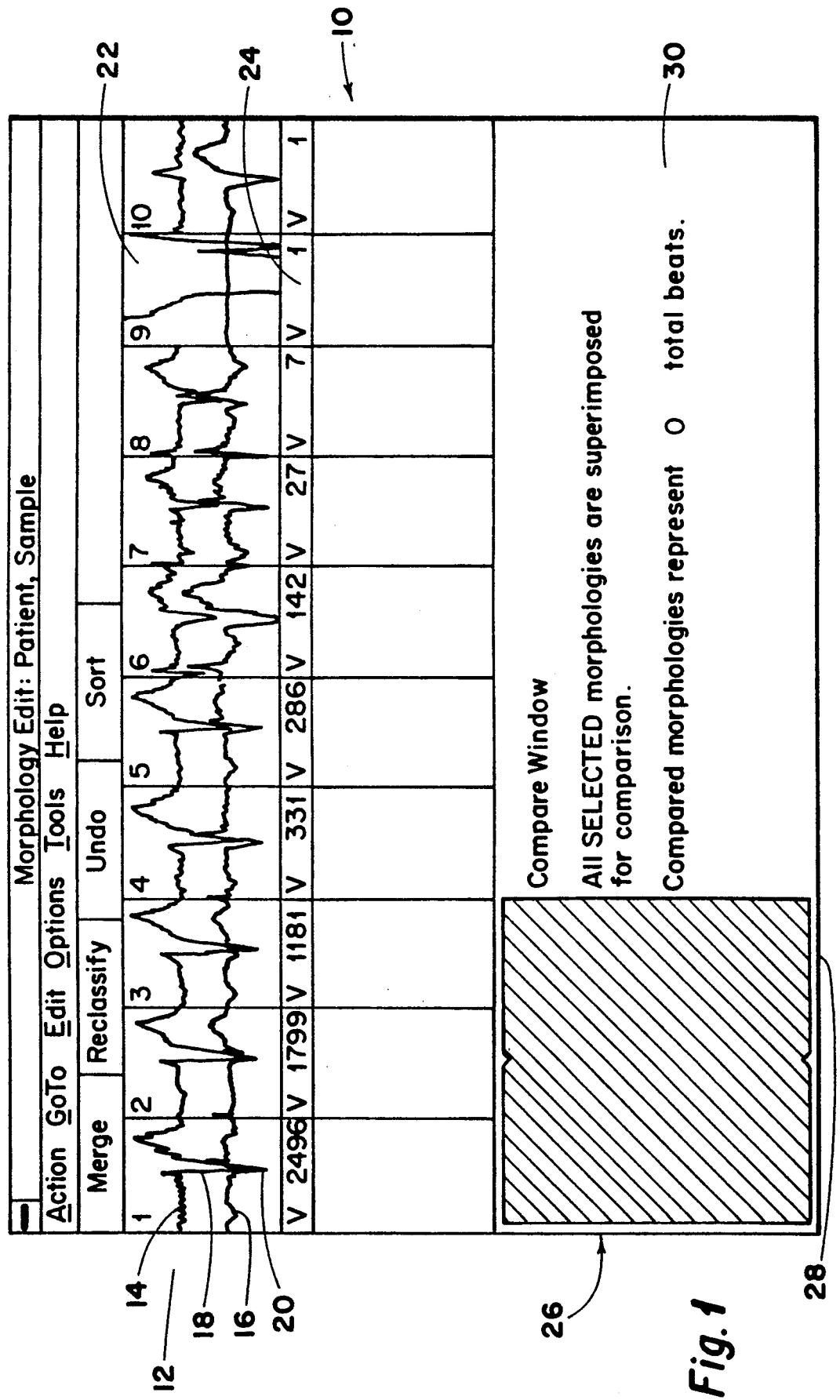
FIG. 1 is a display formed on a cathode ray tube (CRT) screen pursuant to present invention, and indicating ten morphologies into which stored ECG data is initially classified.

Turning now to FIG. 1, indicated generally at 10, is a display formed on a CRT screen incorporated into a system constructed in accordance with the present invention. The present embodiment of the invention comprises a personal computer having an Intel TM 386 processor, a keyboard, a color VGA monitor, a mouse, and a Microsoft Windows 3.0 TM graphical user interface. The computer is programmed, in a manner which is described in more detail hereinafter, to operate in accordance with the following description of the preferred embodiment.

Prior to describing the manner in which the computer program represented by the chart of FIG. 6 controls the system, description will first be made of the user interface and of the manner in which the present embodiment is used to display heartbeat waveforms contained in stored ECG data.

The stored ECG data to be analyzed is collected by a Holter monitor which is fitted to a patient for detecting and storing a continuous ECG waveform for many hours. Often, two vectors are used so that the monitor stores two simultaneously-generated continuous ECG waveforms. Some such monitors are equipped with processors for performing automated preliminary analysis of the ECG heartbeat waveforms as they are stored. For example, each heartbeat waveform is assigned to a morphology classification, such as ventricular ectopic beat, dominant beat, pace beat, artifact, etc. In addition, a heartbeat waveform which is representative of the heartbeat waveforms in each morphology is identified. The number of heartbeat waveforms in each morphology is also computed. A peak detector algorithm locates the R-wave of each heartbeat waveform. The Holter monitor processor also assigns a time of occurrence (in hours, minutes and seconds), from the inception of monitoring, to the R-wave of each heartbeat waveform. The continuous ECG waveform, comprised of a plurality of individual heartbeat waveforms, is stored in chronological order.

CRT display screen 10 has stored ECG waveforms represented thereon in accordance with the present invention. The waveforms on screen 10 were generated by a patient as described above. The collected data along with the information generated by the preliminary analysis performed by the Holter monitor is transferred, in a known manner, to the system in which screen 10 is incorporated.

In FIG. 1, screen 10 includes a plurality of display windows, numbered 1-10 in the upper left corner of each window, indicated generally at 12. Although there are a total of twenty display windows, only 10 have waveforms displayed therein because this is the number of morphologies into which all of the collected heartbeat waveforms were sorted by the Holter monitor. Each display window includes two heartbeat waveforms, like waveforms 14, 16 in display window 1. In the present embodiment of the invention, the Holter monitor records two leads from the patient thereby generating two continuous ECG waveforms. Waveform 14 appeared on one lead and waveform 16 appeared on the other at the same time. The waveforms were selected by the monitor processor to represent a typical waveform in the morphology to which waveforms 14, 16 are assigned. Reference herein to a single waveform includes, in the case where two or more leads of ECG data are collected, any waveforms simultaneously generated on another lead. Each of display windows 2-10 also includes a waveform taken from each lead at the same time which is representative of the morphology to which the waveform was assigned by the Holter monitor processor. Waveforms 14, 16 each include an R-wave 18, 20, respectively.

Each display window includes a waveform window and a data window, like waveform window 22 and data window 24 in display window 9. Each of the data windows, like data window 24, includes two sets of data: a) on the right, a number indicative of the number of beats in the beat classification created by the Holter monitor and represented by the beat in the associated waveform window; and b) on the left, a symbol, in the present example the letter V, which is the beat classification label for the class represented by the waveform in the associated waveform window.

The different types of beat classifications are indicated in the Reclassify panel, which will be described in more detail hereinafter, in FIG. 5. The six beat classifications provided by the present embodiment of the invention are as follows:

| RECLASSIFY PANEL SYMBOL | BEAT CLASSIFICATION |
| --- | --- |
| V | Ventricular Ectopic Beat |
| N | Dominant Beat |
| S | Premature Dominant Beat of Supraventricular Origin |
| P | Paced Beat |
| ? | Possible Ventricular Ectopic Beat |
| A | Artifact |

In the example of FIG. 1, each of the beats is classified into a different morphology of a ventricular ectopic beat.

Figure 2:
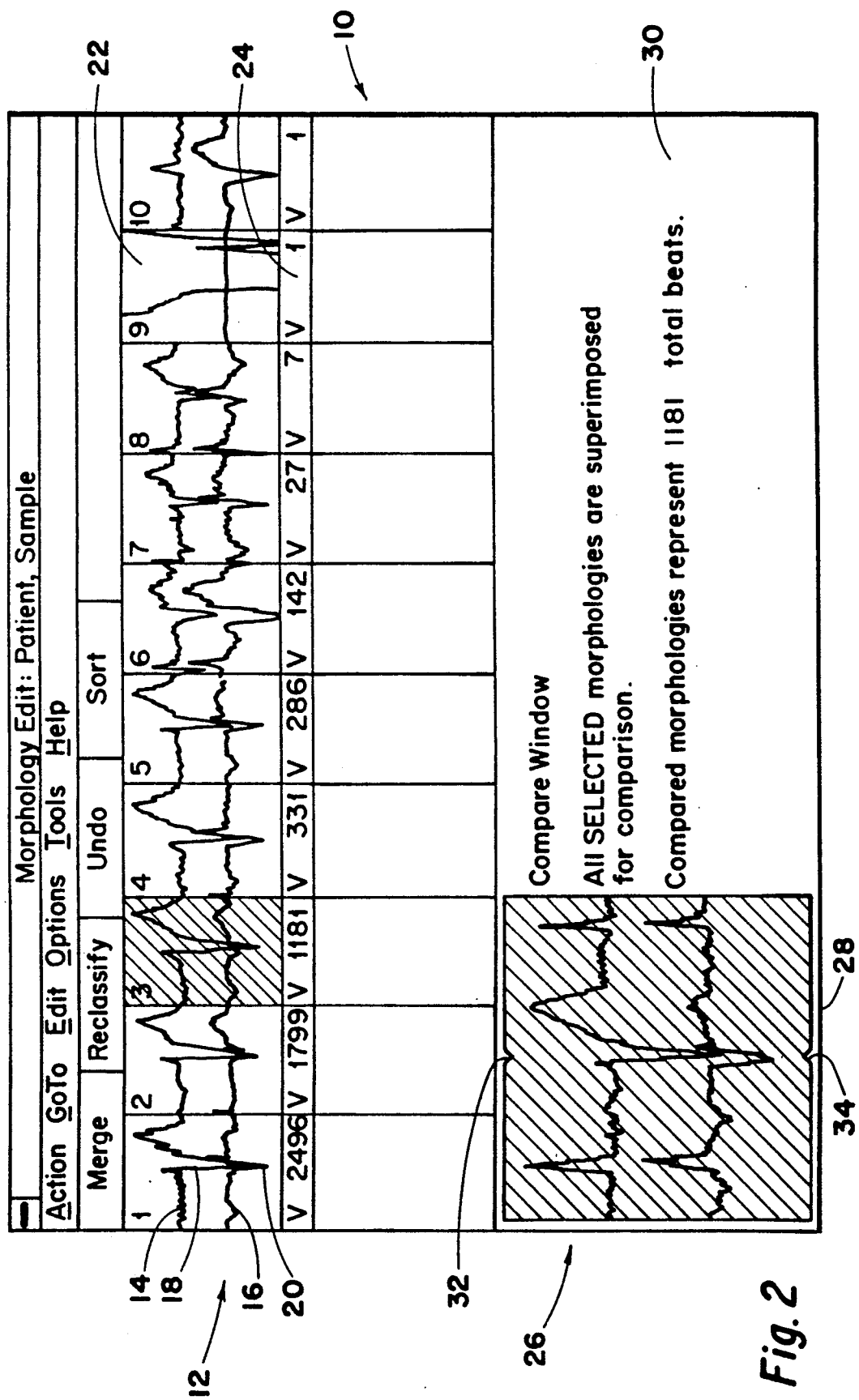
FIG. 2 is a view similar to FIG. 1 indicating one of the ten morphologies selected.

Indicated generally at 26 is a compare window. Like the display windows, compare window 26 includes a waveform window 28 and a data window 30. Turning now to FIG. 2, waveform window 28 includes therein a duplicate of the waveform in display window 3 with the representation of the waveform in window 28 being amplified in both the magnitude (vertical) and time (horizontal) scales. To display one of the waveforms depicted in display windows 1-10 in window 28, the waveform in the display window must be selected. As mentioned above, the computer incorporated into the present embodiment of the invention includes a mouse. As is known in the art, the mouse controls a cursor which moves on CRT screen 10 responsive to mouse movement. To select one of display windows 12, the cursor is positioned thereon and the mouse clicked. Clicking the mouse is referred to herein as an operator signal. Positioning the cursor on a display window and clicking the mouse is referred to herein as selecting a display window. To deselect a selected window, the mouse is again positioned on the window and clicked.

As seen in FIG. 2, display window 28 includes a downwardly-directed pointer 32 aligned with an upwardly-directed pointer 34. An axis connecting the two divides screen 28 in half. The R-wave of the waveform displayed in window 28 is aligned with pointers 32, 34, i.e., on the axis connecting the pointers. As can be seen by comparing the depiction of the waveform in window 28 with the depiction in display window 3, additional portions of the continuous ECG waveform both to the right and left of that visible in display window 3 appear in compare window 28. Thus, not only is the scale enlarged in window 28 but additional data to the left and right of the selected waveform appears.

Figure 3:
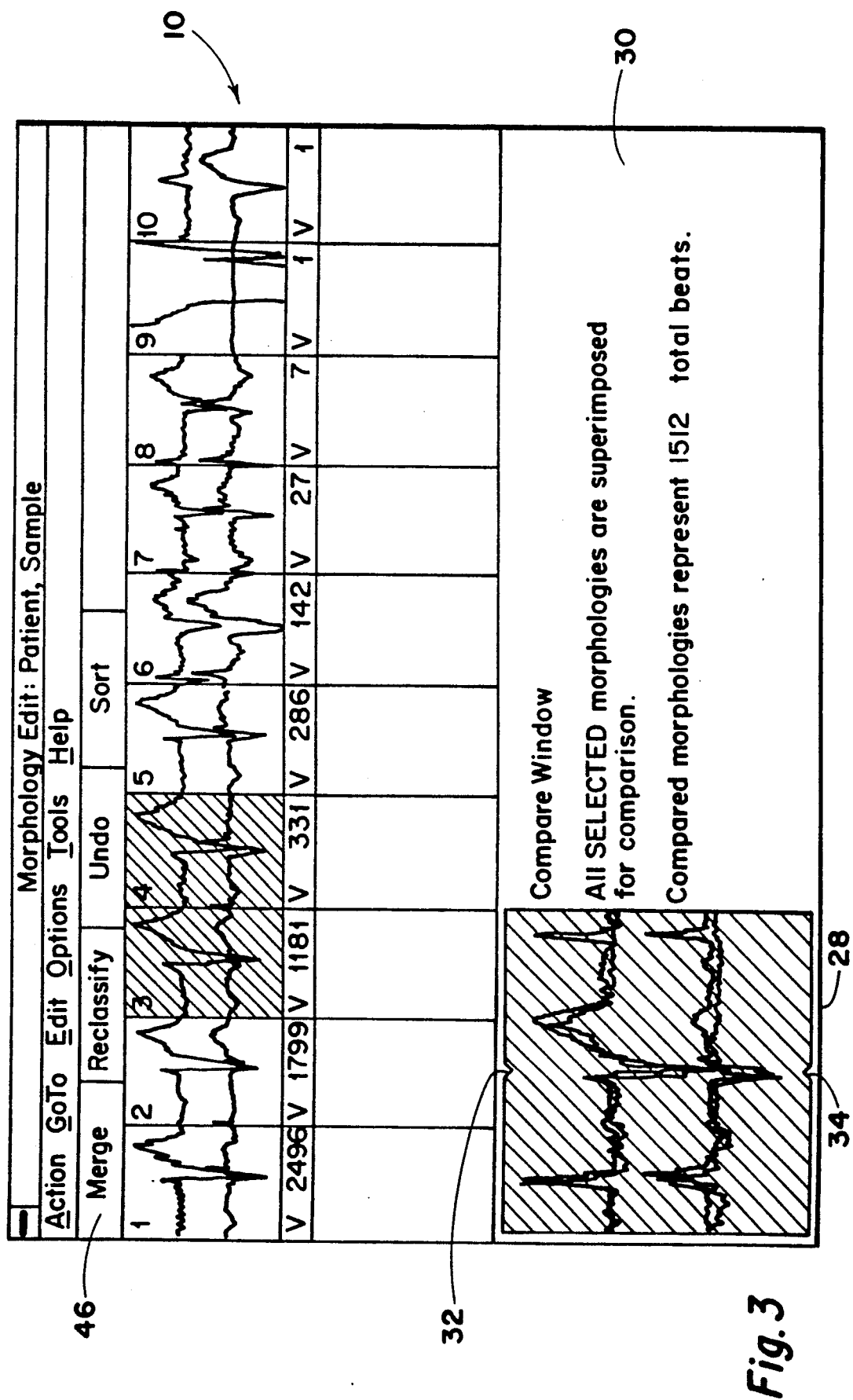
FIG. 3 is a view similar to FIG. 1 indicating two of the ten morphologies selected.

Turning now to FIG. 3, illustrated therein is a depiction of CRT screen 10 in which both display windows 3, 4 are selected as described above. As can be seen, an enlarged-scale version of the waveform in display window 4 is superimposed in compare window 28 over the previously-displayed waveform. The version of the waveform from display window 4 appearing in compare window 28 also includes additional data to the right and left of the view of display window 4. The R-wave of both waveforms in compare window 28 are aligned with pointers 32, 34 and therefore with each other. Although not apparent from the accompanying drawing, the present embodiment of the invention displays the two waveforms in window 28 in different colors so that they may be readily compared and contrasted.

Data window 30 now indicates the total number of heartbeats represented by the compared morphologies in window 28 as 1512. This is the sum of each morphology indicated in the data windows associated with each of display windows 3, 4, i.e., 1181+331=1512.

Figure 4:
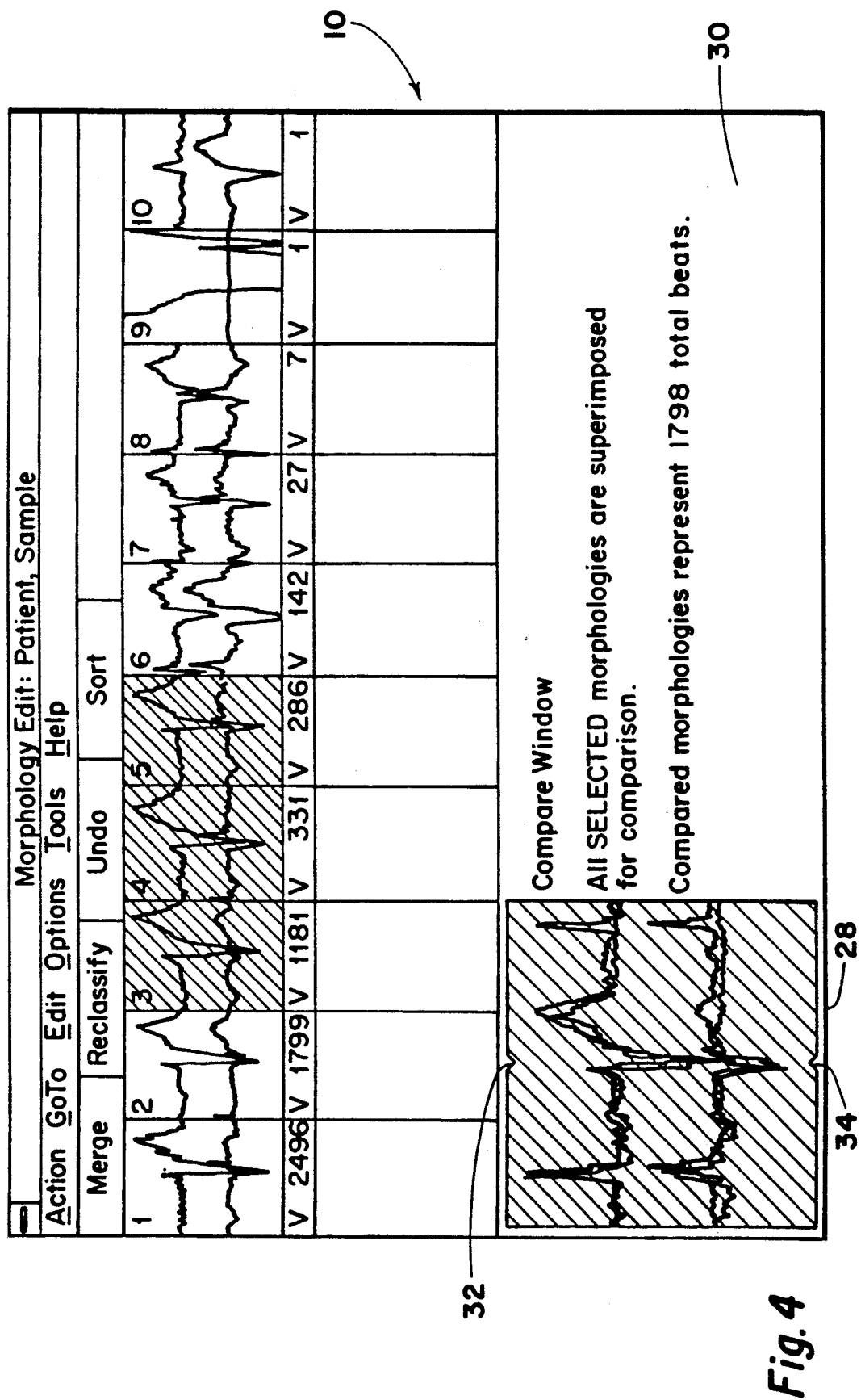
FIG. 4 is a view similar to FIG. 1 indicating three of the ten morphologies selected.

Turning now to FIG. 4, display window 5 is shown selected as described above thus superimposing a third heartbeat waveform in window 28. Like the other two waveforms, the waveform from display window 5 is enlarged in scale and includes additional information from the ECG waveform to the left and right of the heartbeat waveform seen in display window 5. The new waveform in window 28 has, as do the other two waveforms, its R-wave aligned with pointers 32, 34. The third waveform is further displayed in a third color different from either of the colors of the two waveforms previously displayed in window 28. Thus, all three waveforms may be readily compared and contrasted. Data window 30 now indicates that the compared morphologies represent 1798 total beats which is the sum of each of the morphologies represented in display windows 3, 4, 5.

Figure 5:
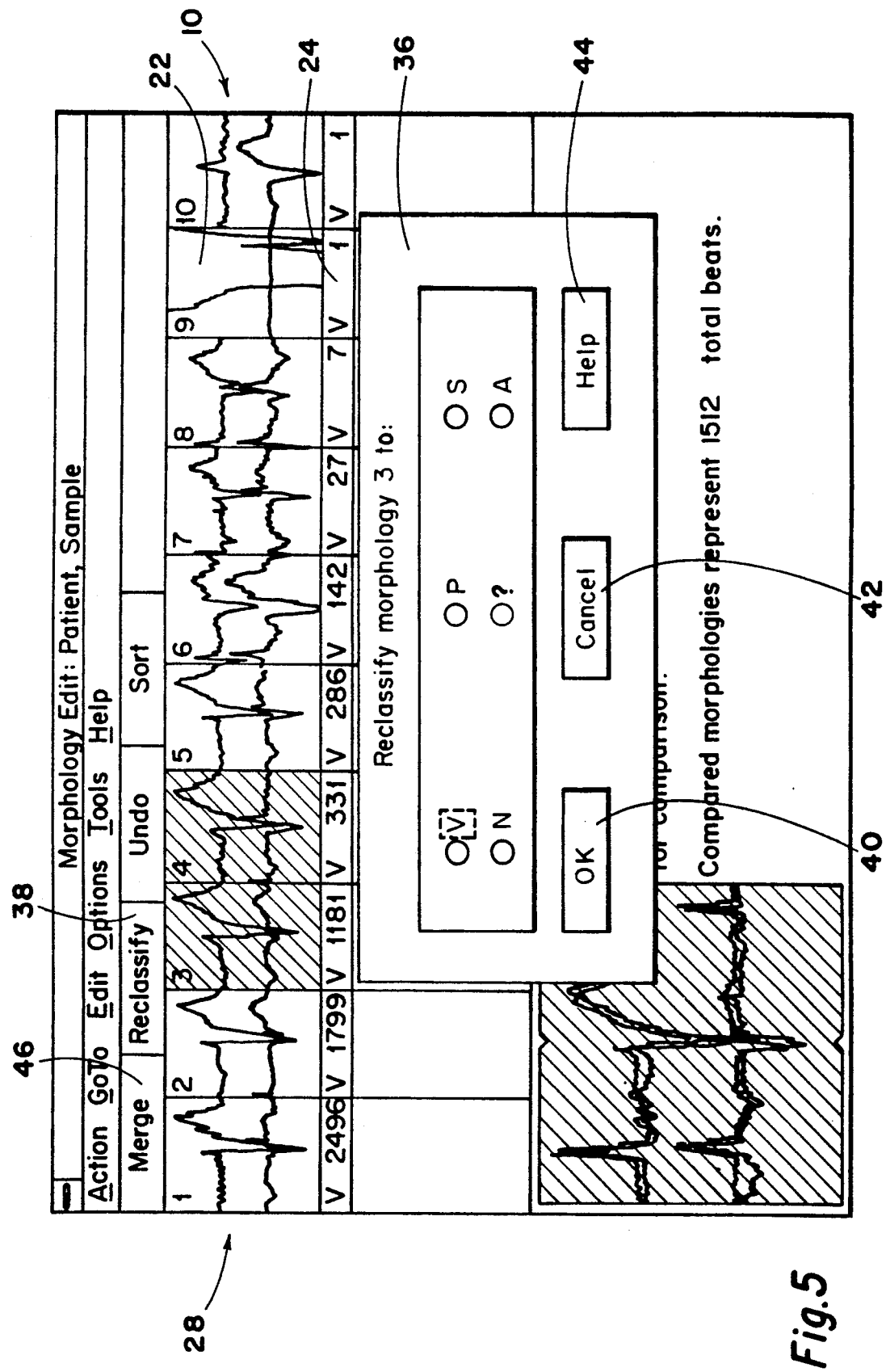
FIG. 5 is a view similar to FIG. 3 with the Reclassify panel open.

Turning now to FIG. 5, CRT screen 10 is shown with display windows 3, 4 selected and with a reclassified panel 36 open. The reclassify panel opens responsive to an operator selecting a reclassify button 38 in the same manner that one of display windows 12 is selected, i.e., a cursor (not shown) is positioned over button 38 via the mouse and the mouse is clicked. Such action causes the reclassify panel to appear as shown in FIG. 5.

When panel 36 initially appears, it is operable to reclassify the morphology or morphologies displayed in compare window 26. With the panel open, the mouse can be used to select a different classification by selecting a different one of the six symbols in the panel which correspond to the classification set forth in the chart above. For example, if a clinician considering the heartbeat waveforms displayed as shown in FIG. 3 determines that the morphologies represented by the waveforms in compare window 26 (those from display windows 3, 4) are actually dominant beats, a symbol N in the reclassification panel is selected thus reclassifying the 1181 heartbeats in the morphology of display window 3 and the 331 heartbeats in the morphology of display window 4. When such occurs the V in the data window of display windows 3, 4 changes to an N to indicate the new morphology. OK button 40 on the reclassify panel makes the change after the new morphology is selected with the cursor and mouse. Cancel button 32 closes the morphology panel and help button 44 displays information (not shown) about operating the system.

If it is desirable to change the classification of a morphology represented in a different display window, the cursor is positioned in the display window and clicked to display only that waveform in compare window 26. The panel is then used to reclassify as described above. As a short cut, the cursor is positioned in the data window associated with the display window and the mouse is clicked. This causes reclassify panel 36 to become operable to change the classification represented by the heartbeat waveform above the data window which is clicked. For example, if it is desired to reclassify the morphology represented by the heartbeat waveform in display window 9, the cursor is positioned on data window 24 and the mouse is clicked. The message at the top of panel 36 then reads: *Reclassify morphology 9 to:*.

A clinician observing CRT screen 10 as shown in FIG. 3 may conclude that the morphologies shown in display windows 3, 4 are not truly different but are examples of the same morphology. If so, the clinician selects a merge button 46 thereby combining the morphologies represented by display windows 3, 4 into a single morphology having 1512 total beats. When such occurs, display window 3 remains as shown but the number 1181 in the associated data window changes to 1512. After selecting merge button 46, display window 4 is empty.

As used with reference to the preferred embodiment, the reclassify and merge operations are as described above. In the claims, however, the terms classify and reclassify are used in their broadest sense and also encompass the merge operation.

Figure 6:
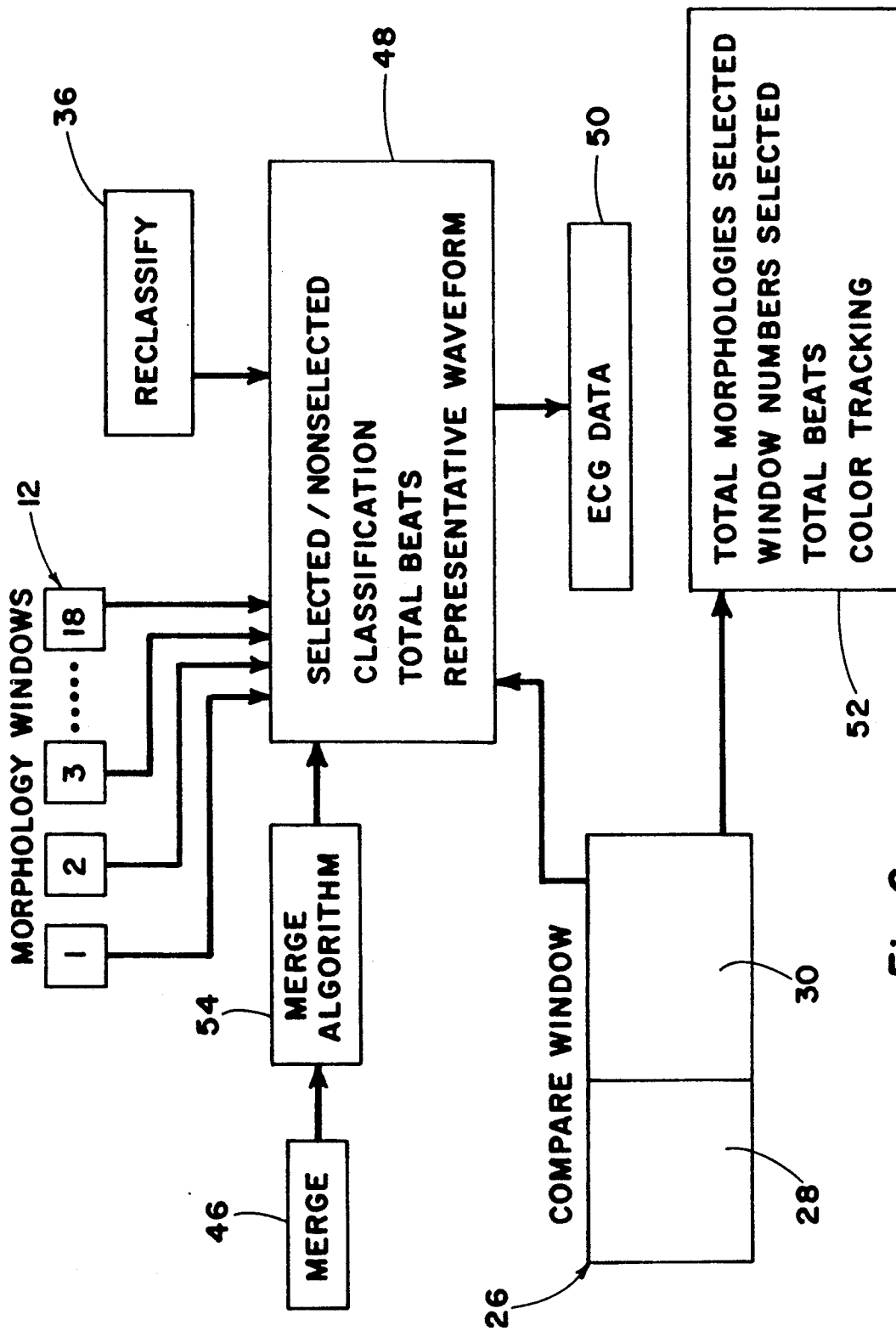
FIG. 6 is a chart depicting the structure of a computer program which in part implements the present embodiment of the invention.

Turning now to FIG. 6, illustrated therein is a chart which depicts operation of a program used to control the computer in the present embodiment of the invention. The program depicted in FIG. 6 was written in C, a language used in the present embodiment of the invention to implement an object-oriented design. The program was written for use with Windows 3.0 ™, supplied by Microsoft Corporation, using the developer's tool provided for use in writing programs compatible with the Windows 3.0 ™ graphical user interface. The terms used in the following description are those used by persons having ordinary skill in the design and implementation of computer programs.

In FIG. 6, structure which is previously identified in the application retains the same numeral for the schematic representation thereof in FIG. 6. It should be appreciated that the display windows, including each waveform window and data window, like waveform window 22 and data window 24 in display window 9, are implemented by a single set of computer code but are illustrated as separate windows in the chart of FIG. 6. Each of the eighteen windows includes an associated data structure, like data structure 48. Although only one data structure is shown, each of the eighteen windows has a separate data structure associated with the code which generates the windows. Each data structure includes the following information: whether the window is selected or nonselected, the classification of the morphology represented by the heartbeat waveform displayed in the window, the total number of heartbeats in that morphology and a representative waveform selected from the heartbeat waveforms in the morphology. Each of the data structures, like data structure 48 and the associated code implementing the eighteen display windows are known in the art as an object. It will be recalled that the classification, computation of total beats in each class and selection of a representative waveform is accomplished by the Holter monitor prior to transfer of data to the computer which implements the present embodiment of the invention.

The display window object, i.e., the code implementing the display windows and the associated data structure, like data structure 48, for each window is linked to a data structure 50 which comprises all of the continuous ECG waveform data provided by the Holter monitor, including morphology classification of each beat and the time of occurrence of the R-wave of each beat.

Another object, comprising a compare window object, includes a set of code implementing compare window 26 and an associated data structure 52. Data structure 52 includes the total morphologies, i.e., display windows, selected; the number of each selected display window; the total heartbeats in all of the selected morphologies; and information relating to the color of each waveform in compare window 28.

The merge algorithm 54 determines which of the selected morphologies each of the other selected morphologies is merged into when merge button 46 is selected. (It also prevents merging two or more morphologies in different classes). In the present embodiment of the invention, the waveform representing the selected morphology having the largest classification initially assigned by the Holter processor remains in its display window with the other morphologies being merged therewith. After the merge operation, the other selected display windows change so that no waveform or data is displayed.

In operation, when one of display windows 12 is selected as described above, its status in the data structure associated therewith, like data structure 48, changes from nonselected to selected. This causes the display window to highlight, like display windows 3, 4 in FIG. 3, in a known manner. Because the object comprising compare window 26 and its associated data structure 52 points to each of the display window data structures, like data structure 48, the compare window object obtains information concerning the status, i.e., selected versus nonselected, of each window. As described above, each representative waveform is provided to compare window 28 which displays the same in an enlarged scale. Also, the total beats from data structure 52 is provided to data window 30 for display therein. Color tracking information in data structure 52 assigns a color to each waveform displayed in window 28. The present embodiment of the invention can display waveforms in three different colors. When more than three colors are selected, the color tracking information in data structure 52 assigns the original color, i.e., that assigned to the first displayed waveform, to the fourth waveform and so forth in a repeating pattern.

When the clinician determines that two of the waveforms under observation should be merged, button 46 is selected thereby causing merge algorithm 54 to retain one of the morphologies displayed in display windows 12 and to lump the total beats of the selected windows into that morphology. Both the waveform and data are removed from the other selected display windows. Information concerning the new classification of the reclassified heartbeat waveforms is provided to each of the heartbeat waveforms in data structure 50.

Similarly, when a morphology is reclassified using reclassify panel 36 as described above, the classification in the associated data structure, like data structure 48, is changed responsive to information from the reclassify panel. The new classification is further provided, as in the case of merged classes, to data structure 50 so that each of heartbeat waveforms in the class is assigned to the new class selected in panel 36.

Having illustrated and described the principles of my invention in a preferred embodiment thereof, it should be readily apparent to those skilled in the art that the invention can be modified in arrangement and detail without departing from such principles.

We claim all modifications coming within the spirit and scope of the accompanying claims:

1. A method for classifying heartbeat waveforms contained in stored ECG data comprising the steps of:
   displaying a heartbeat waveform in each of a plurality of display windows;
   selecting two of the display windows;
   displaying the heartbeat waveforms in the selected display windows superimposed in a compare window; and
   classifying the heartbeat waveform in one of the selected windows.

2. The method of claim 1 wherein the step of displaying the heartbeat waveforms in the selected display windows superimposed in a compare window comprises the step of displaying one of the waveforms in one color and the other waveform in another color.

3. The method of claim 1 wherein the heartbeat waveforms displayed in the display windows are each representative of a class of similar heartbeat waveforms and wherein the step of classifying the heartbeat waveform in one of the selected windows comprises the step of merging the classes represented by the heartbeat waveforms in the selected windows.

4. The method of claim 1 wherein said method further includes the step of selecting a third display window.

5. The method of claim 1 wherein the step of selecting two of the display windows comprises the steps of placing a cursor on the selected display window and generating an operator signal.

6. The method of claim 1 wherein the heartbeat waveforms displayed in the display windows are each representative of a class of similar heartbeat waveforms and wherein the step of classifying the heartbeat waveform in one of the selected windows comprises the step of changing the classification of the class represented by the heartbeat waveform in one of the selected windows.

7. The method of claim 1 wherein the step of displaying the heartbeat waveforms in the selected display windows superimposed in a compare window comprises the step of displaying the heartbeat waveforms with their R waves aligned.

8. The method of claim 1 wherein the step of displaying the heartbeat waveforms in the selected display windows superimposed in a compare window further comprises the step of displaying the waveforms in the compare window in an enlarged scale from that of the display windows.

9. A method for examining ECG data of the type containing heartbeat waveforms classified into a plurality of morphologies comprising the steps of:
   identifying a heartbeat waveform representative of each morphology;
   displaying each identified heartbeat waveform in a different display window;
   selecting a plurality of the display windows;
   displaying the heartbeat waveforms in the selected display windows superimposed in a compare window; and
   reclassifying the morphologies represented by the waveforms in the compare window.

10. The method of claim 9 wherein the step of displaying the heartbeat waveforms in the selected display windows superimposed in a compare window comprises the step of displaying the heartbeat waveforms in different colors.

11. The method of claim 9 wherein the step of reclassifying the morphology represented by one of the waveforms in the compare window comprises the step of merging the morphology represented by one of the waveforms in the compare window with the morphology represented by another of the displayed waveforms.

12. The method of claim 9 wherein the step of selecting a plurality of the display windows comprises the step of placing a cursor on each selected window and substantially simultaneously generating an operator signal.

13. The method of claim 9 wherein the step of reclassifying the morphology represented by one of the waveforms in the compare window comprises the step of changing the class of the morphologies represented by the waveforms in the compare window.

14. The method of claim 9 wherein the step of displaying the heartbeat waveforms in the selected display windows superimposed in a compare window comprises the step of displaying the heart beat waveforms with their R waves aligned.

15. The method of claim 9 wherein the step of displaying the heartbeat waveforms in the selected display windows superimposed in a compare window comprises the step of displaying the heart beat waveforms in the compare window in an enlarged scale from that of the display windows.

16. Apparatus for classifying heartbeat waveforms contained in stored ECG data comprising:
- a plurality of display windows for displaying heartbeat waveforms;
- means for displaying a heartbeat waveform in each of the display windows;
- means for selecting two of the display windows;
- a compare window for displaying heartbeat waveforms;
- means for displaying the heartbeat waveforms in the selected display windows superimposed in the compare window; and
- means for classifying the heartbeat waveforms in the compare window.

17. The apparatus of claim 16 wherein said means for displaying the heartbeat waveforms in the selected display windows superimposed in the compare window further comprises means for displaying one of the waveforms in one color and the other waveform in another color.

18. The apparatus of claim 16 wherein said means for selecting two of the display windows comprises means for positioning a cursor on said display windows.

19. The apparatus of claim 16 wherein said compare window has a larger scale than said display windows.

20. The apparatus of claim 16 wherein said means for displaying the heartbeat waveforms in the selected display windows superimposed in the compare window further comprises means for displaying the heartbeat waveforms with their R waves aligned.

* * * * *